United States Patent
Ungaro Pinto Coelho et al.

(10) Patent No.: US 12,318,190 B2
(45) Date of Patent: Jun. 3, 2025

(54) MAGNETOMETERLESS DETECTION OF INCORRECT ATTACHMENT AND CALIBRATION OF MOTION TRACKING SYSTEM

(71) Applicant: SWORD HEALTH, S.A., Oporto (PT)

(72) Inventors: Luís Ungaro Pinto Coelho, Oporto (PT); Marta Maria Ramalho Ferreira, Oporto (PT); Ana Clara Ferreira Matos, Oporto (PT); Pedro Henrique Oliveira Santos, Oporto (PT); Virgílio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 0 days.

(21) Appl. No.: 17/824,742

(22) Filed: May 25, 2022

(65) Prior Publication Data

US 2022/0291252 A1    Sep. 15, 2022

Related U.S. Application Data

(63) Continuation of application No. 17/417,211, filed as application No. PCT/PT2018/050044 on Dec. 26, 2018.

(51) Int. Cl.
*A61B 5/11*       (2006.01)
*G01C 25/00*    (2006.01)
*G01P 15/18*    (2013.01)

(52) U.S. Cl.
CPC ............ *A61B 5/1114* (2013.01); *G01P 15/18* (2013.01); *G01C 25/00* (2013.01)

(58) Field of Classification Search
CPC .......... G01P 15/18; G01C 21/16; G01C 25/00
See application file for complete search history.

(56) References Cited

U.S. PATENT DOCUMENTS 5,440,484 A * 8/1995 Kao ...................... G01C 17/38
                                                    701/530
6,820,025 B2   11/2004 Bachmann et al.
(Continued)

FOREIGN PATENT DOCUMENTS

EP        3586745 A1    1/2020
PT        110804 A      12/2019
(Continued)

OTHER PUBLICATIONS

Machine translation of WO2018210469A1 (Year: 2018).*
(Continued)

*Primary Examiner* — Lee E Rodak
*Assistant Examiner* — Sangkyung Lee
(74) *Attorney, Agent, or Firm* — SCHWEGMAN LUNDBERG & WOESSNER, P.A.

(57) ABSTRACT

A method for adjusting operation of a motion tracking system includes a computing apparatus and sensors, each sensor having a gyroscope and an accelerometer. The method includes the steps of aligning the sensors; providing, each sensor to the computing apparatus, a first orientation when the sensors are aligned, the first orientation having a first heading; placing the sensors on a person; and providing, each sensor to the computing apparatus, a second orientation when the sensors are placed on the person, the second orientation having a second heading. The method further includes digitally determining, the computing apparatus, whether the sensors are placed on the person according to a predetermined sensor arrangement based on both the first and second headings of each sensor; and adjusting, the computing apparatus, the operation of the motion tracking system based on the determination. Also, a system for tracking motion of a person.

18 Claims, 8 Drawing Sheets

(56) References Cited

U.S. PATENT DOCUMENTS

| | | | |
|---|---|---|---|
| 10,045,439 | B2 | 8/2018 | Longinotti-Buitoni et al. |
| 10,393,542 | B2 | 8/2019 | Funk et al. |
| 11,372,484 | B2 | 6/2022 | Branquinho Gomes et al. |
| 11,609,102 | B1 | 3/2023 | Santos et al. |
| 11,720,185 | B2 | 8/2023 | Branquinho Gomes et al. |
| 11,726,165 | B1 | 8/2023 | Santos et al. |
| 2003/0023192 | A1* | 1/2003 | Foxlin .................. A61B 5/7242 600/595 |
| 2005/0215888 | A1* | 9/2005 | Grimm .................. A61B 90/39 606/130 |
| 2007/0287911 | A1* | 12/2007 | Haid ...................... A61B 90/36 606/130 |
| 2011/0275957 | A1* | 11/2011 | Bhandari .............. A61B 5/1114 600/595 |
| 2012/0140202 | A1* | 6/2012 | Rothenberger ........... G06T 7/33 356/4.01 |
| 2014/0303524 | A1 | 10/2014 | Chen et al. |
| 2016/0330586 | A1 | 11/2016 | Venkatraman et al. |
| 2017/0307403 | A1 | 10/2017 | Funk et al. |
| 2018/0000367 | A1* | 1/2018 | Longinotti-Buitoni ..................... A41D 13/1281 |
| 2018/0070864 | A1* | 3/2018 | Schuster .............. A61B 5/1128 |
| 2018/0095492 | A1 | 4/2018 | Matloff |
| 2019/0212359 | A1* | 7/2019 | Erivantcev .............. G06F 3/017 |
| 2020/0005926 | A1 | 1/2020 | António Ferro Bento et al. |
| 2022/0026461 | A1 | 1/2022 | Ungaro Pinto Coelho et al. |
| 2023/0003528 | A1 | 1/2023 | Santos et al. |
| 2023/0003863 | A1 | 1/2023 | Alves et al. |
| 2023/0166155 | A1 | 6/2023 | Coelho Alves et al. |

FOREIGN PATENT DOCUMENTS

| | | | | |
|---|---|---|---|---|
| WO | WO-02093272 | A1 | | 11/2002 |
| WO | WO-2013057622 | A1 | | 4/2013 |
| WO | WO-2013059246 | A1 | | 4/2013 |
| WO | WO-2018210469 | A1 | * | 11/2018 ............. A61B 5/112 |
| WO | WO-2018210520 | A1 | * | 11/2018 ........... A61B 5/1114 |
| WO | WO-2019224279 | A1 | | 11/2019 |
| WO | WO-2019243438 | A1 | | 12/2019 |
| WO | WO-2020049097 | A1 | | 3/2020 |
| WO | WO-2020115251 | A1 | | 6/2020 |
| WO | WO-2020127246 | A1 | | 6/2020 |
| WO | WO-2020139093 | A1 | | 7/2020 |
| WO | WO-2020200891 | A1 | | 10/2020 |
| WO | WO-2020221704 | A1 | | 11/2020 |
| WO | WO-2020249514 | A1 | | 12/2020 |
| WO | WO-2021048022 | A1 | | 3/2021 |
| WO | WO-2021089407 | A1 | | 5/2021 |
| WO | WO-2021130324 | A1 | | 7/2021 |
| WO | WO-2021180869 | A1 | | 9/2021 |
| WO | WO-2021259688 | A1 | | 12/2021 |
| WO | WO-2022167582 | A1 | | 8/2022 |
| WO | WO-2022207485 | A1 | | 10/2022 |

OTHER PUBLICATIONS

Machine translation of WO2018210520A1 (Year: 2018).*

PCT/PT2018/050044 International Search Report and Written Opinion dated Feb. 10, 2019.

Roetenberg et al.: Xsens MVN: Full 6DOF human motion tracking using miniature inertial sensors. Xsens Motion Technologies BV, pp. 1-9 [retrieved online at CiteSeer on May 13, 2022] doi10.1.1.569.9604 (2009).

U.S. Appl. No. 17/417,211 Non-Final Office Action mailed Sep. 27, 2022.

U.S. Appl. No. 17/417,211 Final Office Action dated May 1, 2023.

U.S. Appl. No. 17/417,211 Non-Final Office Action dated Sep. 12, 2023.

U.S. Appl. No. 17/417,211, Applicant Interview Summary filed Sep. 28, 2023, 2 pgs.

U.S. Appl. No. 17/417,211, Examiner Interview Summary mailed Apr. 20, 2023, 2 pgs.

U.S. Appl. No. 17/417,211, Examiner Interview Summary mailed Dec. 14, 2023, 2 pgs.

U.S. Appl. No. 17/417,211, Preliminary Amendment filed Jun. 22, 2021, 13 pgs.

U.S. Appl. No. 17/417,211, Response filed Mar. 24, 2023 to Non Final Office Action mailed Sep. 27, 2022, 15 pgs.

U.S. Appl. No. 17/417,211, Response filed Jul. 31, 2023 to Final Office Action mailed May 1, 2023, 13 pgs.

U.S. Appl. No. 17/417,211, Response filed Dec. 12, 2023 to Non Final Office Action mailed Sep. 13, 2023, 15 pgs.

U.S. Appl. No. 17/417,211, Supplemental Amendment mailed Apr. 14, 2023, 17 pgs.

European Application Serial No. 18842485.7. Response filed Jun. 3, 2022 to Communication Under Rule 71(3) EPC mailed Mar. 24, 2022, 8 pgs.

International Application Serial No. PCT/PT2018/050044, International Preliminary Report on Patentability mailed Jul. 8, 2021, 7 pgs.

U.S. Appl. No. 17/417,211, Advisory Action mailed Mar. 21, 2024, 3 pgs.

U.S. Appl. No. 17/417,211, Final Office Action mailed Jan. 17, 2024, 52 pgs.

U.S. Appl. No. 17/417,211, Non Final Office Action mailed May 3, 2024, 60 pgs.

U.S. Appl. No. 17/417,211, Response filed Mar. 12, 2024 to Final Office Action mailed Jan. 17, 2024, 19 pgs.

U.S. Appl. No. 17/417,211, Response filed Apr. 5, 2024 to Advisory Action mailed Mar. 21, 2024, 19 pgs.

U.S. Appl. No. 17/417,211, Response filed Jul. 31, 2024 to Non Final Office Action mailed May 3, 2024, 16 pgs.

U.S. Appl. No. 17/417,211, Final Office Action mailed Aug. 15, 2024, 66 pgs.

* cited by examiner

MAGNETOMETERLESS DETECTION OF INCORRECT ATTACHMENT AND CALIBRATION OF MOTION TRACKING SYSTEM

CROSS-REFERENCE TO RELATED APPLICATIONS

This application is a continuation of U.S. application Ser. No. 17/417,211, filed on Jun. 22, 2021, which is a U.S. National Phase Application under 35 U.S.C. § 371 of International Application No. PCT/PT2018/050044, filed internationally on Dec. 26, 2018, all of which are hereby incorporated by reference in their entireties.

TECHNICAL FIELD

The present invention relates to the field of motion tracking systems. More specifically, the present invention relates to attachable or wearable motion tracking systems that do not require measurements of magnetometers for calibration thereof and/or detecting that sensors thereof have not been accurately placed on a person to be tracked.

STATE OF THE ART

Motion tracking technologies can be mainly divided into two groups: a first group of systems that have a number of devices that must be attached to the person to be tracked, particularly sensors to be attached to the person, and a second group of systems that track the motion of the person with no device being attached to the person, thus they mainly rely on sensors such as cameras.

Concerning the motion tracking systems of the first group, the sensors are to be attached or worn by a person that usually moves many different ways. The accurateness of the motion tracked depends upon the errors in the measurements of the different sensors, therefore making the sensors to measure the magnitudes as accurately as possible or knowing how to reduce the errors in the measurements is very important.

Another issue that affects the accurateness of the motion tracked in some cases is the variation between the expected positions where the sensors are to be attached to the person and the actual positions where the sensors are attached to the person; not only the position affects the motion tracked, but also the orientations of the sensors.

Some attachable or wearable motion tracking systems include sensors having magnetometers. By means, inter alia, of the magnetic fields measured by the magnetometers the motion of the person may be tracked. However, both the existence of magnetic disturbances and the increase in differences in the measurements of the magnetometers over time result in erroneous motion tracking in many occasions.

Accordingly, there is an interest in providing a method for detecting whether sensors of a motion tracking system are accurately placed on a person and calibrating said motion tracking system so that a more accurate motion tracking may be achieved, whereby said detection and calibration do not require measurements of magnetometers.

DESCRIPTION OF THE INVENTION

A first aspect of the invention refers to a method for adjusting operation of a motion tracking system comprising a computing apparatus and a plurality of sensors, each sensor comprising a gyroscope and an accelerometer, the method comprising: aligning the plurality of sensors; providing, each sensor of the plurality of sensors to the computing apparatus, a first orientation when the sensors are aligned, the first orientation comprising a first heading; placing the plurality of sensors on a person; providing, each sensor of the plurality of sensors to the computing apparatus, a second orientation when the sensors are placed on the person, the second orientation comprising a second heading; digitally determining, the computing apparatus, whether the plurality of sensors is placed on the person according to a predetermined sensor arrangement based on both the first and second headings of each sensor of the plurality of sensors; and adjusting, the computing apparatus, the operation of the motion tracking system based on the determination.

The computing apparatus is capable of determining whether the sensors of the motion tracking system have been correctly placed on the person, with respect to the predetermined sensor arrangement, so that the motion of the person can be accurately tracked.

The computing apparatus relies on the measurements provided by the sensor fusion algorithm of each sensor, whereby the measurements of the gyroscope and the accelerometer are combined so as to provide a measurement taking into account the precision of each sensing device. The sensor fusion algorithm usually also takes into account the precision of the sensing devices as the time passes, hence said algorithm may partially or completely disregard measurements of particular sensing devices after some time has elapsed since their last calibration, as the error cumulates over time faster for some types of sensing devices than for others. The particular ways in which the sensor fusion algorithm may process the measurements and combine them are disclosed in the prior art as the skilled person is well aware.

The sensors are aligned one with respect to each other so that the first orientations provided by the sensors correspond to measurements made when all the sensors are arranged having fixed relative orientations. As the sensors are aligned, the first headings provided by the sensors are indicative of any deviation in the measurements of the sensors. In the context of the present disclosure, aligning the sensors refers to arranging the sensors according to a known set of orientations of the sensors (for example a predetermined set of orientations) so that it may be determined what is the deviation between the actual heading of the sensor and the heading measured by the sensor. Preferably, but not necessarily, the sensors are aligned such that they are all facing the same direction, however in some examples one or more sensors may be aligned with respect to other one or more sensors even if they are not facing the same direction; this is so as long as it can be determined what is the direction each sensor is facing and, thus, the deviation between the actual heading and the measured heading can be determined for each sensor.

The sensors are placed on the person so that motion thereof may be tracked. The sensors are to be placed on the person in accordance with the predetermined sensor arrangement, which depends upon the particular type of motion to be tracked, hence different types of motion to be tracked may result in different predetermined sensor arrangements as the limbs to be tracked are different or, alternatively, the same limbs are to be tracked but with different orientations of the sensors; it may also occur that different types of motion are to be tracked with the same predetermined arrangement of sensors. The predetermined sensor arrangement(s) is stored in the computing apparatus, particularly in at least one memory thereof, which provides the computing apparatus with data relative to how the sensors are to be placed on the person.

The procedure by which the person knows how the sensors have to be put thereon may be carried out in a number of ways. For example, the computing apparatus may output information or instructions (e.g. on a screen, acoustically, etc.) for the user (the same person to be tracked or a different person) to indicate how each particular sensor is to be placed in accordance with the predetermined sensor arrangement. As another example, the sensors are placed on the person in accordance with the predetermined sensor arrangement and the user inputs in the computing apparatus, by means of user input means (e.g. tactile screen, keyboard, mouse, etc.), the correspondence between each sensor on the person and the sensors of the predetermined sensor arrangement registered in the computing apparatus. As a further example, the sensors may be provided with an attachment interface for attaching each to a strap; the straps are used for attaching the sensors on the person. The attachment interface is connected to a unique identifiable element present in the strap, which is an electronic component such as a resistor with a specific resistance value in each strap. The attachment interface is coupled or connected to the processor thereof (e.g. a microcontroller), the latter continuously measuring the resistance value at the terminals of the attachment interface. According to the measured resistance value, the sensor determines to which strap it is attached, and whether it is attached to a strap at all (when the resistance value is an open circuit).

Since the placement of the sensors on the person is prone to errors in the orientations of the sensors, the motion tracking system determines the possible existence of these errors. Particularly, once the sensors are placed on the person, they provide the second orientations that are processed by the computing apparatus. In order to detect and determine whether the sensors are not placed according to the predetermined sensor arrangement, each possible pair of the second headings is processed and compared with predetermined heading differences that the computing apparatus expects to receive from the sensors; said predetermined heading differences depend on the predetermined sensor arrangement. Owing to the relative differences in the measurements of the sensors, particularly the measurements provided by the sensor fusion algorithms, the first headings are taken into account when the second headings are processed in pairs and compared with the predetermined heading differences so that the relative differences between measurements may be compensated for.

The comparisons are made by computing differences between the pairs of second headings and the expected heading differences. In this sense, the definition of the placement of the sensors in the predetermined sensor arrangement is defined by or allows the derivation of the relative differences between headings of sensors when correctly placed on the body. The computed differences are preferably compared with either a predetermined difference threshold (e.g. 2.5°, 5.0°, 9.0°, 15.0°, etc.) or a pair of predetermined difference thresholds (e.g. −5.0° and 10.0°, 10.0° and −15.0°, etc.), which may be adjusted in the computing apparatus, for instance. The computing apparatus determines that the plurality of sensors is placed on the person according to the predetermined sensor arrangement if the computed differences do not exceed the predetermined difference threshold or the pair of predetermined difference thresholds. For instance, if the predetermined difference threshold is 5.0°, if all the differences between the heading differences of the second headings and the expected heading differences are equal to or less than 5.0°, the computing apparatus determines that the plurality of sensors is correctly placed on the person (i.e. the sensors are arranged according to the predetermined sensor arrangement); if, for instance, the pair of predetermined difference thresholds is −10.0° and 15.0°, this effectively establishes a heading difference range of 25.0° in which a more demanding requirement is defined towards negative heading differences than for positive heading differences (e.g. if the expected heading difference is 90.0°, the computed heading difference shall be within the 80.0° and 105.0° range). Even if the computing apparatus considers that the sensors are placed according to the predetermined sensor arrangement, it may also adjust the operation of the motion tracking system and, thus, it does not only adjust the operation when the sensors are not placed according to the predetermined sensor arrangement.

A time elapsed between the moment that the sensors provide the first orientations and the moment that the sensors provide the second orientations is preferably as reduced as possible, preferably less than 5 minutes, and more preferably less than 3 minutes and/or 1 minute, therefore preferably the sensors are withdrawn from the first device and placed on the body in this time interval. By reducing the time it takes to carry out this process, the lower the error that will affect the measurements of the sensors (which tends to increase over time, for example the drift of the gyroscope will introduce some error in the measurements) and, consequently, the more accurate will be the determination and adjustment of the operation of the motion tracking system.

The computing apparatus adjusts the operation of the motion tracking system in accordance with the determination.

In some embodiments, the step of digitally determining whether the plurality of sensors is placed on the person according to the predetermined sensor arrangement comprises: digitally computing, the computing apparatus, a first transformation for each sensor of the plurality of sensors that aligns the first heading thereof with a first predetermined heading; and digitally processing, the computing apparatus, a third heading of each sensor of the plurality of sensors in order to compute heading differences from all pairs of third headings and determine whether the plurality of sensors is placed on the person according to the predetermined sensor arrangement, each third heading being the second heading of the corresponding sensor with the corresponding first transformation applied thereto.

The computing apparatus digitally computes the first transformation for each of the sensors such that the first transformations, when they are applied to the corresponding orientations provided by the sensors, adjust the heading of each orientation in accordance with the deviation determined owing to the first headings. In this sense, the first transformations make the headings of all the first orientations to be aligned with the first predetermined heading (e.g. any heading value like, for instance, the north, or the first heading of one of the sensors).

As further orientations are provided by the sensors, the corresponding headings are indicative of the change in heading of the different sensors once the first transformation is applied thereto. This is so because the first transformation virtually calibrates the sensors when they have a known orientation relative to the other sensors (because they are aligned). By way of example, if after computing the first transformations one of the sensors is rotated such that the heading thereof changes, the orientations provided after the rotation are processed by the computing apparatus, in particular the heading thereof is obtained and the first transformation is applied thereto; in this example, all but one sensor will have a heading aligned with the first predetermined heading, whereas the remaining sensors will have a heading with an angular difference with respect to the first predetermined heading that is indicative of the amount of rotation that the sensor has been subjected to.

If one or more sensors have the first heading thereof already aligned with the first predetermined heading, the first transformations for these one or more sensors are not computed (and not applied to further orientations) or are computed but they do not modify the orientation (i.e. the transformation keeps the orientation and the heading as they are). A first deviation threshold or range may be established in the computing apparatus whereby a first heading not aligned with the first predetermined heading but which does not exceed the first deviation threshold or is inside the deviation range is considered to be aligned; such first deviation threshold or range has a difference in angle with respect to the first predetermined heading that is preferably less than one degree, for example tenths or hundredths of a degree, e.g. 0.05°, 0.2°, 0.5°, etc.

The computing apparatus applies the first transformations to the second orientations so that the orientation of each sensor has the second heading thereof adjusted with the particular first transformation for each sensor, thereby providing the third headings. The computing apparatus processes the third headings in pairs so as to determine if the plurality of sensors is put on the person according to the predetermined sensor arrangement by comparing the differences resulting from each possible pair of third headings with the heading differences expected if the sensors were put on the person in accordance with the predetermined sensor arrangement. As the first transformations align the headings of the sensors prior to placing them on the person, the computing apparatus determines that any heading difference between the third headings of a pair of sensors and the heading difference expected (based on the predetermined sensor arrangement) is mainly due to an incorrect placement of one or both sensors on the person as the drift error of the gyroscope is negligible.

By way of example, if the heading difference between a pair of third headings is 92.3° and the expected heading difference is 90.0°, the comparison of these values will be 90.0° minus 92.3° (equal to −2.3°), thus the determination of whether the sensors are placed on the person according to the predetermined sensor arrangement will be based on said comparison value.

Further, as aforementioned, preferably the results of these comparisons are further compared with respect to a predetermined difference threshold (e.g. 2.5°, 5.0°, 9.0°, 15.0°, etc.) or a pair of predetermined difference thresholds (e.g. −5.0° and 10.0°, 10.0° and −15.0°, etc.) in order to determine whether the sensors are placed according to the predetermined sensor arrangement. With respect to the former, the predetermined difference threshold sets the range around the expected heading difference, e.g. if the expected heading difference is 90.0° and the predetermined difference threshold is 5.0°, the computed heading difference should be within 90.0° plus-minus ('±') 5.0° (i.e. between 85.0° and 95.0°, thus the comparison value should be between −5.0° and 5.0°). With respect to the latter, each threshold of the pair of predetermined difference thresholds sets the lower limit or the upper limit of the range around the expected heading difference, e.g. if the expected heading difference is 90.0° and the pair of predetermined difference thresholds is −10.0° and 20.0°, the computed heading difference should be within 90.0° minus 10.0°, and 90.0° plus 20.0° (i.e. between 80.0° and 110.0°, thus the comparison value should be between −10.0° and 20.0°).

In some of these embodiments, the step of adjusting the operation of the motion tracking system comprises: digitally computing, the computing apparatus, a second transformation for each sensor of the plurality of sensors that aligns the third heading thereof with a second predetermined heading for the corresponding sensor according to the predetermined sensor arrangement, and digitally applying, the computing apparatus, the second transformations or both the first and second transformations computed to each orientation provided by each sensor of the plurality of sensors to the computing apparatus while motion of the person is tracked with the motion tracking system, or to an algorithm of the computing apparatus for processing the motion of the person tracked with the motion tracking system; and/or providing at least one user perceptible signal indicative of the computing apparatus having determined that at least one sensor of the plurality of sensors is not placed on the person according to the predetermined sensor arrangement.

The computing apparatus adjusts the motion tracking of the system by further calibrating the sensors. To this end, the computing apparatus computes the second transformations that adjust the third heading of the second orientations. In particular, the second transformations align each third heading with the second predetermined heading that is specific for each sensor and which depends upon the predetermined sensor arrangement. The second predetermined headings are established based upon heading differences; for instance, with reference to the above example, the second transformations for the corresponding two sensors are those that make the heading difference of the third headings to be equal to the expected heading difference. As the process is repeated for each possible pair of third headings, the second transformations of the sensors may be progressively adjusted so that, at the end, all pairs of third headings (once adjusted with the respective second transformations) have the heading difference thereof equal to the respective expected heading differences.

The computing apparatus adjusts the motion tracking by applying the second transformations, or alternatively both the first and second transformations, to either the orientations provided by the sensors during the motion tracking procedure or the algorithm of the computing apparatus that processes the motion tracked. In some cases, the first transformation needs not be applied to the orientations because sometimes the measurement differences of the sensors can be compensated for by the algorithm that processes the motion tracking. In some cases, the second transformations or both the first and second transformations are applied to said algorithm so that the motion tracking or the posture of the person tracked may be adjusted, or the person tracked is properly matched to a digital model for representing the motion, etc.

Additionally or alternatively, the user is notified that one or more sensors have not been correctly placed so that the user may adjust the placement of the sensors. Since the computing apparatus may determine which sensor(s) is/are incorrectly placed, or pair of sensors from which one of the sensors is incorrectly placed, in some examples the computing apparatus provides this information so that the user is aware of which sensor or subset of sensors, which are or possibly are incorrectly placed, need to be adjusted. The motion tracking system may be provided with at least one means for providing the at least one user perceptible signal that the computing apparatus operates. Said means may be, for instance but without limitation, a screen, loudspeakers, LEDs, etc.

In some embodiments, the step of digitally determining whether the plurality of sensors is placed on the person according to the predetermined sensor arrangement comprises digitally processing, the computing apparatus, the second heading of each sensor of the plurality of sensors in order to compute heading differences from all pairs of second headings and determine whether the plurality of sensors is placed on the person according to the predetermined sensor arrangement. In these embodiments, the first heading of each sensor is processed such that it adjusts the corresponding heading differences computed or heading differences according to the predetermined sensor arrangement.

Instead of digitally computing the first transformations that virtually calibrate the sensors owing to the known orientation relative to the other sensors, the first headings adjust the values of the heading differences, i.e. the differences between each pair of second headings, or alternatively they adjust the values of the expected (according to the predetermined sensor arrangement) heading differences of the pairs of headings. In both cases, the comparison of the heading differences of the second headings with the expected heading differences implicitly compensates for the relative differences between measurements of the sensors as determined from the first headings.

For example, concerning the first case, if the heading difference between a pair of second headings is 90.5° and the first headings of the corresponding sensors are 3.2° and 1.4°, the difference of these first headings is 1.8°. This value may be for example subtracted from or added to (depending on the reference used, i.e. which direction/sense is considered as positive or negative) the heading difference, thus providing a heading difference of 90.5° minus 1.8° (equal to 88.7°) or 90.5° plus 1.8° (equal to 92.3°). If the expected heading difference is 90.0°, the comparison of this value with the adjusted heading difference will be 90.0° minus 88.7° (equal to 1.3°) or 90.0° minus 92.3° (equal to −2.3°), depending on the reference used as aforementioned, thus the determination of whether the sensors are placed on the person according to the predetermined sensor arrangement will be based on said comparison value.

For example, concerning the latter case, using the same values of the above example, the expected heading difference has its value adjusted in accordance with the difference between the first headings, thus being 90.0° minus 1.8° (equal to 88.2°) or 90.0° plus 1.8° (equal to 91.8°), again depending on the reference used. The heading differences of the second headings are then compared with one of these values, i.e. 88.2° minus 90.5° (equal to −2.3°) and 91.8° minus 90.5° (equal to 1.3°). The same results are obtained in both cases.

Even though the above examples are described with sums and subtractions, it is readily apparent that the present disclosure is not limited to these mathematical operations and, therefore, different mathematical operations that result in analogous adjustments and comparisons are also possible within the scope of the present disclosure.

Further, as aforementioned, preferably the results of these comparisons are further compared with respect to a predetermined difference threshold (e.g. 2.5°, 5.0°, 9.0°, 15.0°, etc.) or a pair of predetermined difference thresholds (e.g. −5.0° and 10.0°, 10.0° and −15.0°, etc.) in order to determine whether the sensors are placed according to the predetermined sensor arrangement.

In some of these embodiments, the step of adjusting the operation of the motion tracking system comprises: digitally computing, the computing apparatus, a first transformation for each sensor of the plurality of sensors that aligns the second heading thereof with a first predetermined heading for the corresponding sensor according to both the predetermined sensor arrangement and the first heading, and digitally applying, the computing apparatus, the first transformations computed to each orientation provided by each sensor of the plurality of sensors to the computing apparatus while motion of the person is tracked with the motion tracking system, or to an algorithm of the computing apparatus for processing the motion of the person tracked with the motion tracking system; and/or providing at least one user perceptible signal indicative of the computing apparatus having determined that at least one sensor of the plurality of sensors is not placed on the person according to the predetermined sensor arrangement.

The computing apparatus adjusts the motion tracking of the system by further calibrating the sensors. To this end, the computing apparatus computes the first transformations that adjust the second heading of the second orientations. In particular, the first transformations align each second heading with the first predetermined heading that is specific for each sensor and which depends upon the predetermined sensor arrangement. The first predetermined headings are established based upon heading differences; the first transformations for two sensors are those that make the heading difference of the second headings to be equal to the expected heading difference. As the process is repeated for each possible pair of second headings, the first transformations of the sensors may be progressively adjusted so that, at the end, all pairs of second headings (once adjusted with the respective first transformations) have the heading difference thereof equal to the respective expected heading differences. The first transformations are computed taken into account the first headings so that a single transformation per sensor calibrates the measurements thereof. The computing apparatus adjusts the motion tracking by applying the first transformations to either the orientations provided by the sensors during the motion tracking procedure or the algorithm of the computing apparatus that processes the motion tracked.

Additionally or alternatively, the user is notified that one or more sensors have not been correctly placed so that the user may adjust the placement of the sensors.

In some embodiments, the second orientations are provided by the plurality of sensors while the person has a predetermined posture.

The sensors provide the orientations that the computing apparatus uses for determining whether the placement of the sensors does not match the predetermined sensor arrangement while the person has the predetermined posture, for instance standing with a straight posture, the arms being alongside the body, the legs being side-by-side, combinations thereof, etc.

When the person has the predetermined posture, the determination made by the computing apparatus is more accurate because no heading variations are due to a posture that the person has at a particular moment. Accordingly, the operation of the motion tracking system is also adjusted more accurately when the person has the predetermined posture.

In some embodiments, each sensor of the plurality of sensors further comprises a magnetometer; and the method further comprises, prior to the step of placing the plurality of sensors on the person: not processing measurements of the magnetometers in a sensor fusion algorithm of each sensor of the plurality of sensors; or reducing a weight of the measurements of the magnetometers in the sensor fusion algorithm of each sensor of the plurality of sensors.

Sensors of motion tracking systems usually include magnetometers whose measurements are used for tracking the motion of the target. The magnetic fields measured, however, are subject to magnetic disturbances that affect the measurements, thereby worsening the performance of the motion tracking system as the motion is not properly tracked.

The computing apparatus commands the sensors not to process the measurements of the magnetometers in the sensor fusion algorithms thereof. Alternatively, the computing apparatus command the sensors to reduce the weight of the measurements of the magnetometers so that their influence on the measurements provided by the sensor fusion algorithm is reduced. Accordingly, the measurements of the sensor fusion algorithms are mainly driven by the gyroscope and the accelerometer.

In some of these embodiments, the measurements of the magnetometers are normally processed by the sensor fusion algorithm in order to provide the first orientations. That is to say, the first headings provided by the sensors make use of measurements of the magnetometers, yet the measurements of the magnetometers are not processed or the weight thereof is reduced when the sensors are to be placed on the person.

In some of these embodiments, the step of not processing the measurements of the magnetometers or the step of reducing the weight of the measurements of the magnetometers takes place also prior to the step of providing, each sensor of the plurality of sensors to the computing apparatus, the first orientation. That is to say, the first headings provided by the sensors neither make use of measurements of the magnetometers or have the weight thereof reduced for the provision of both the first and second orientations and, thus, both the first and second headings.

In some embodiments, the method further comprises digitally computing, the computing apparatus, heading differences from all pairs of first headings; and digitally processing, the computing apparatus, the computed heading differences of the first headings in order to determine if one or more sensors of the plurality of sensors are aligned such that they have a 180° heading rotation with respect to the other sensor of the plurality of sensors. In these embodiments, the computing apparatus both digitally determines whether the plurality of sensors is placed on the person according to the predetermined sensor arrangement and adjusts the operation of the motion tracking system if each computed heading difference of the first headings fulfills the following: a modulus of the heading difference is less than or equal to a predetermined validation threshold; or a modulus of 180° minus the heading difference is less than or equal to the predetermined validation threshold.

Depending on the cover and/or the aspect of the sensors, even if each sensor is aligned with respect to each other such that, for example, all sensors are apparently facing the same direction, it may occur that one or more sensors are flipped with respect to the other sensors, namely they are rotated 180° with respect to the other sensors. This, in turn, results in a 180° rotation of the heading measured by the sensor(s). The computing apparatus may however detect such 180° rotation of the heading measured by computing the two moduli. To this end, the computing apparatus computes the heading differences between each pair of first headings, i.e. it computes the relative difference between one first heading and another first heading, and uses said heading differences to determine whether one sensor is flipped with respect to another sensor.

If the first modulus is less than or equal to the predetermined validation threshold, the two sensors are facing the same direction according to the measured headings, whereas if the second modulus is less than or equal to the predetermined validation threshold, the two sensors are facing opposite directions (i.e. 180° difference in the direction) according to the measured headings. In particular, the computed heading differences are compared with 180° plus-minus ('±') a predetermined validation threshold. If a computed heading difference falls within the range 180° minus the predetermined validation threshold and 180° plus the predetermined validation threshold, it is considered that the one sensor is rotated 180° with respect to the other. By way of example, the predetermined validation threshold is an angle value or represents an angle value of 20°, 30°, 40°, 45°, etc. which may be configured in the computing apparatus, for instance.

If there is a heading difference that exceeds the predetermined validation threshold, in particular by comparing it either with or without a 180° rotation resulting from a possible flipped alignment of the sensors, the computing apparatus determines that there are significant errors in the measurements provided by the sensors. Accordingly, the computing apparatus does not carry out the digital determination and the adjustment of the operation of the motion tracking system until all heading differences fulfill one of the aforementioned criteria.

In these cases, usually a complete calibration of the motion tracking system is necessary whereby the sensors are fully calibrated so that the measurements thereof feature lower errors. These situations may also be due to faulty sensors, thus a user may be aware of possible problems in the motion tracking system as the computing apparatus does not proceed further with the motion tracking procedure.

In some embodiments, the computing apparatus adjusts the operation of the motion tracking system if at least one computed heading difference of the first headings does not fulfill the following: a modulus of the heading difference is less than or equal to a predetermined validation threshold; or a modulus of 180° minus the heading difference is less than or equal to the predetermined validation threshold; the operation of the motion tracking system being adjusted such that it provides at least one user perceptible signal indicative of the computing apparatus having determined that at least one computed heading difference of the first headings does not fulfill any one of the above criteria.

When at least one heading difference exceeds the predetermined validation threshold, either when it is compared with the 180° heading rotation or without it, the computing apparatus commands the provision of the at least one user perceptible signal so that the user is notified of the errors in the measurements of the sensors and, thus, the user may take corrective action.

In some embodiments, the step of aligning the plurality of sensors comprises: providing a first device comprising at least one cavity adapted for introduction of one or more sensors of the plurality of sensors; and introducing each sensor of the plurality of sensors into the first device.

The first device comprises the at least one cavity dimensioned such that one or more sensors fit therein when the sensors are introduced with a particular orientation so that all sensors may be arranged similarly. The at least one cavity may be a single cavity in which two or more sensors of the plurality of sensors may be introduced side-by-side such that the two or more sensors have fixed relative orientations (so that each sensor does not change its orientation with respect to the other sensors); to this end, the single cavity may include one or more spacing elements that provide a gap between each pair of sensors. The at least one cavity may also be a plurality of cavities, in each of which one sensor may be introduced.

The sensors are introduced into the first device for alignment thereof so that the first orientations provided by the sensors correspond to measurements made when all the sensors are arranged having fixed relative orientations. Owing to the arrangement of the sensors in the first device, the first headings provided by the sensors are indicative of any deviation in the measurements of the sensors.

In some cases, the at least one cavity allows the introduction of the sensors such that one or more sensors are flipped 180° with respect to other sensors. In these cases, when the computing apparatus digitally processes the computed heading differences of the first headings, it determines whether one or more sensors of the plurality of sensors have been introduced in the first device with a 180° heading rotation with respect to the other sensor of the plurality of sensors introduced in the first device.

In some other embodiments, the step of aligning the plurality of sensors comprises arranging or attaching the plurality of sensors on a surface having indicated thereon a predetermined set of orientations of the sensors. These indications may be attachable elements, drawn elements or the like that, for instance, show the contours or the appearance that the sensors shall have when they are arranged on the surface so that they are aligned, particularly aligned in accordance with the predetermined set of orientations. When the plurality of sensors is to be attached to said surface, the sensors may be provided with attaching means such as a mechanical clip, Velcro, etc. and, preferably, the surface is also provided with attaching means that cooperate with the attaching means of the sensors.

In some other embodiments, the step of aligning the plurality of sensors comprises attaching the plurality of sensors one to another such that they are aligned. To this end, the sensors may be provided with attaching means such as a mechanical clip, Velcro, etc.

A second aspect of the invention relates to a system for tracking motion of a person, the system comprising: a plurality of sensors, each sensor comprising a gyroscope and an accelerometer; and a computing apparatus comprising at least one processor, at least one memory and means for transmitting and receiving data; each sensor of the plurality of sensors being configured to provide, to the computing apparatus, a first orientation when the sensors are aligned, and a second orientation when the sensors are placed on the person, the first and second orientations comprising first and second headings, respectively; and the computing apparatus being programmed to: digitally determine whether the plurality of sensors is placed on the person according to a predetermined sensor arrangement based on both the first and second headings of each sensor of the plurality of sensors; and adjust an operation of the system based on the determination.

The system is capable of both tracking the motion of the person and adjusting the operation thereof without the need for measurements of magnetometers, which in many occasions are not accurate enough for motion tracking purposes due to magnetic disturbances.

The computing apparatus, by means of the at least one processor and the at least one memory, processes the first and second headings of the plurality of sensors in order to determine whether the sensors are placed on the person according to the predetermined sensor arrangement, which is stored in the computing apparatus. As aforementioned, different predetermined sensor arrangements are possible since they relate to the motions to be tracked.

When the sensors are aligned, the first headings thereof reveal the deviations between the measurements of the sensors. Afterwards, when the sensors are placed on the person, by means of the second headings the computing apparatus determines if the sensors are placed according to the predetermined sensor arrangement; in order to perform such determination, the computing apparatus takes into account the deviations between the measurements of the sensors derived from the first headings. The computing apparatus bases the determination on comparisons between heading differences derivable from the second headings and expected heading differences (defined by or derivable from the predetermined sensor arrangement). The results of these comparisons are, preferably, compared with a predetermined difference threshold, e.g. 2.5°, 5.0°, 9.0°, 15.0°, etc. or a pair of predetermined difference thresholds (e.g. −5.0° and 10.0°, 10.0° and −15.0°, etc.), which may be adjusted in the computing apparatus.

In some embodiments, the computing apparatus is programmed to digitally determine whether the plurality of sensors is placed on the person according to the predetermined sensor arrangement by: digitally computing a first transformation for each sensor of the plurality of sensors that aligns the first heading thereof with a first predetermined heading; and digitally processing a third heading of each sensor of the plurality of sensors in order to compute heading differences from all pairs of third headings and determine whether the plurality of sensors is placed on the person according to the predetermined sensor arrangement, each third heading being the second heading of the corresponding sensor with the corresponding first transformation applied thereto.

In some of these embodiments, the computing apparatus is programmed to adjust the operation of the system by: digitally computing a second transformation for each sensor of the plurality of sensors that aligns the third heading thereof with a second predetermined heading for the corresponding sensor according to the predetermined sensor arrangement, and digitally applying the second transformations or both the first and second transformations computed to each orientation provided by each sensor of the plurality of sensors to the computing apparatus, or to an algorithm of the computing apparatus for processing the motion of the person tracked with the motion tracking system; and/or providing at least one user perceptible signal indicative of the computing apparatus having determined that at least one sensor of the plurality of sensors is not placed on the person according to the predetermined sensor arrangement, the system comprising at least one means for providing the at least one user perceptible signal.

The at least one means comprise, for instance but without limitation, one or more of: a screen, loudspeakers, LEDs, etc.

In some embodiments, the computing apparatus is programmed to digitally determine whether the plurality of sensors is placed on the person according to the predetermined sensor arrangement by digitally processing the second heading of each sensor of the plurality of sensors in order to compute heading differences from all pairs of second headings and determine whether the plurality of sensors is placed on the person according to the predetermined sensor arrangement. In these embodiments, the first heading of each sensor is processed such that it adjusts the corresponding heading differences computed or heading differences according to the predetermined sensor arrangement.

In some of these embodiments, the computing apparatus is programmed to adjust the operation of the system by: digitally computing a first transformation for each sensor of the plurality of sensors that aligns the second heading thereof with a first predetermined heading for the corresponding sensor according to both the predetermined sensor arrangement and the first heading, and digitally applying the first transformations computed to each orientation provided by each sensor of the plurality of sensors to the computing apparatus, or to an algorithm of the computing apparatus for processing the motion of the person tracked with the motion tracking system; and/or providing at least one user perceptible signal indicative of the computing apparatus having determined that at least one sensor of the plurality of sensors is not placed on the person according to the predetermined sensor arrangement, the system comprising at least one means for providing the at least one user perceptible signal (e.g. one or more of: a screen, loudspeakers, LEDs, etc.).

In some embodiments, each sensor of the plurality of sensors further comprises a magnetometer; and the computing apparatus is further programmed to command each sensor of the plurality of sensors to configure a sensor fusion algorithm thereof such that the sensor fusion algorithm: does not process the measurements of the magnetometer; or reduces a weight of the measurements of the magnetometer; and the computing apparatus is further programmed to command each sensor of the plurality of sensors to provide the second orientation or both the first and second orientations after configuring the sensor fusion algorithm thereof.

The computing apparatus reconfigures the sensors such that the sensor fusion algorithms thereof do not take into account the measurements of the magnetometers, or that the relevance of such measurements in the orientations provided is reduced. This reconfiguration takes place either: before the sensors are placed on the person, particularly when the sensors are still aligned, so that the second orientations do not depend upon or depend less on the measurements of the magnetometers; or even before the sensors provide the first orientations so that neither the first orientations nor the second orientations depend upon or depend less on the measurements of the magnetometers.

In some embodiments, the computing apparatus is further programmed to: digitally compute heading differences from all pairs of first headings; and digitally process the computed heading differences of the first headings in order to determine if one or more sensors of the plurality of sensors are aligned such that they have a 180° heading rotation with respect to the corresponding other sensor of the plurality of sensors. In these embodiments, the computing apparatus is programmed to both digitally determine whether the plurality of sensors is placed on the person according to the predetermined sensor arrangement and adjust the operation of the system if each computed heading difference of the first headings fulfills the following: a modulus of the heading difference is less than or equal to a predetermined validation threshold; or a modulus of 180° minus the heading difference is less than or equal to the predetermined validation threshold.

In some embodiments, the computing apparatus is further programmed to adjust the operation of the motion tracking system if at least one computed heading difference of the first headings does not fulfill the following: a modulus of the heading difference is less than or equal to a predetermined validation threshold; or a modulus of 180° minus the heading difference is less than or equal to the predetermined validation threshold. In these embodiments, the operation of the motion tracking system is adjusted such that it provides at least one user perceptible signal indicative of the computing apparatus having determined that at least one computed heading difference of the first headings does not fulfill the criteria.

In some embodiments, the system further comprises a device comprising at least one cavity adapted for introduction of one or more sensors of the plurality of sensors.

In some embodiments, each sensor of the plurality of sensors further comprises attaching means (e.g. a mechanical clip, Velcro, etc.).

Similar advantages as those described with respect to the first aspect of the invention are also applicable to second aspect of the invention.

A third aspect of the invention relates to a computer program product that has instructions which, when executed by a computing device, cause the computing device to perform the steps of: receiving first orientations from a plurality of sensors of a motion tracking system when they are aligned, each first orientation comprising a first heading; receiving second orientations from the plurality of sensors when they are placed on a person, each second orientation comprising a second heading; digitally determining whether the plurality of sensors is placed on the person according to a predetermined sensor arrangement based on both the first and second headings of each sensor of the plurality of sensors; and adjusting operation of the motion tracking system based on the determination.

In some embodiments, digitally determining whether the plurality of sensors is placed on the person according to the predetermined sensor arrangement comprises: digitally computing a first transformation for each sensor of the plurality of sensors that aligns the first heading thereof with a first predetermined heading; and digitally processing a third heading of each sensor of the plurality of sensors in order to compute heading differences from all pairs of third headings and determine whether the plurality of sensors is placed on the person according to the predetermined sensor arrangement, each third heading being the second heading of the corresponding sensor with the corresponding first transformation applied thereto.

In some of these embodiments, adjusting the operation of the motion tracking system comprises: digitally computing a second transformation for each sensor of the plurality of sensors that aligns the third heading thereof with a second predetermined heading for the corresponding sensor according to the predetermined sensor arrangement, and digitally applying the second transformations or both the first and second transformations computed to each orientation received from each sensor of the plurality of sensors while motion of the person is tracked with the motion tracking system, or to an algorithm of the computing device for processing the motion of the person tracked with the motion tracking system; and/or providing at least one user perceptible signal indicative of having determined that at least one sensor of the plurality of sensors is not placed on the person according to the predetermined sensor arrangement.

In some embodiments, digitally determining whether the plurality of sensors is placed on the person according to the predetermined sensor arrangement comprises digitally processing the second heading of each sensor of the plurality of sensors in order to compute heading differences from all pairs of second headings and determine whether the plurality of sensors is placed on the person according to the predetermined sensor arrangement. In these embodiments, the first heading of each sensor is processed such that it adjusts the corresponding heading differences computed or heading differences according to the predetermined sensor arrangement.

In some of these embodiments, adjusting the operation of the motion tracking system comprises: digitally computing a first transformation for each sensor of the plurality of sensors that aligns the second heading thereof with a first predetermined heading for the corresponding sensor according to both the predetermined sensor arrangement and the first heading, and digitally applying the first transformations computed to each orientation received from each sensor of the plurality of sensors while motion of the person is tracked with the motion tracking system, or to an algorithm of the computing device for processing the motion of the person tracked with the motion tracking system; and/or providing at least one user perceptible signal indicative of having determined that at least one sensor of the plurality of sensors is not placed on the person according to the predetermined sensor arrangement.

In some embodiments, each sensor of the plurality of sensors comprises a gyroscope and an accelerometer.

In some of these embodiments, each sensor of the plurality of sensors further comprises a magnetometer. In these embodiments, the instructions further cause the computing device to command each sensor of the plurality of sensors to configure a sensor fusion algorithm thereof such that the sensor fusion algorithm: does not process measurements of the magnetometer; or reduces a weight of the measurements of the magnetometer.

In some of these embodiments, the instructions further cause the computing device to command each sensor of the plurality of sensors to provide the second orientation or both the first and second orientations after configuring the sensor fusion algorithm thereof.

In some embodiments, the instructions further cause the computing device to: digitally compute heading differences from all pairs of first headings; and digitally process the computed heading differences of the first headings in order to determine if one or more sensors of the plurality of sensors are aligned such that they have a 180° heading rotation with respect to the other sensor of the plurality of sensors. In these embodiments, the instructions cause the computing device to both digitally determine whether the plurality of sensors is placed on the person according to the predetermined sensor arrangement and adjust the operation of the motion tracking system if each computed heading difference of the first headings fulfills the following: a modulus of the heading difference is less than or equal to a predetermined validation threshold; or a modulus of 180° minus the heading difference is less than or equal to the predetermined validation threshold In some embodiments, the instructions cause the computing device to adjust the operation of the motion tracking system if at least one computed heading difference of the first headings does not fulfill the following: a modulus of the heading difference is less than or equal to a predetermined validation threshold; or a modulus of 180° minus the heading difference is less than or equal to the predetermined validation threshold; the operation of the motion tracking system being adjusted such that it provides at least one user perceptible signal indicative of having determined that at least one computed heading difference of the first headings does not fulfill any one of the above criteria.

A fourth aspect of the invention relates to a data stream which is representative of a computer program product according to the third aspect of the invention.

A fifth aspect of the invention relates to a computer-readable storage medium having stored therein a computer program product according to the third aspect of the invention.

Similar advantages as those described with respect to the first aspect of the invention are also applicable to the third, fourth and fifth aspects of the invention.

BRIEF DESCRIPTION OF THE DRAWINGS

To complete the description and in order to provide for a better understanding of the invention, a set of drawings is provided. Said drawings form an integral part of the description and illustrate embodiments of the invention, which should not be interpreted as restricting the scope of the invention, but just as examples of how the invention can be carried out. The drawings comprise the following figures.

DESCRIPTION OF WAYS OF CARRYING OUT THE INVENTION

Figure 1:
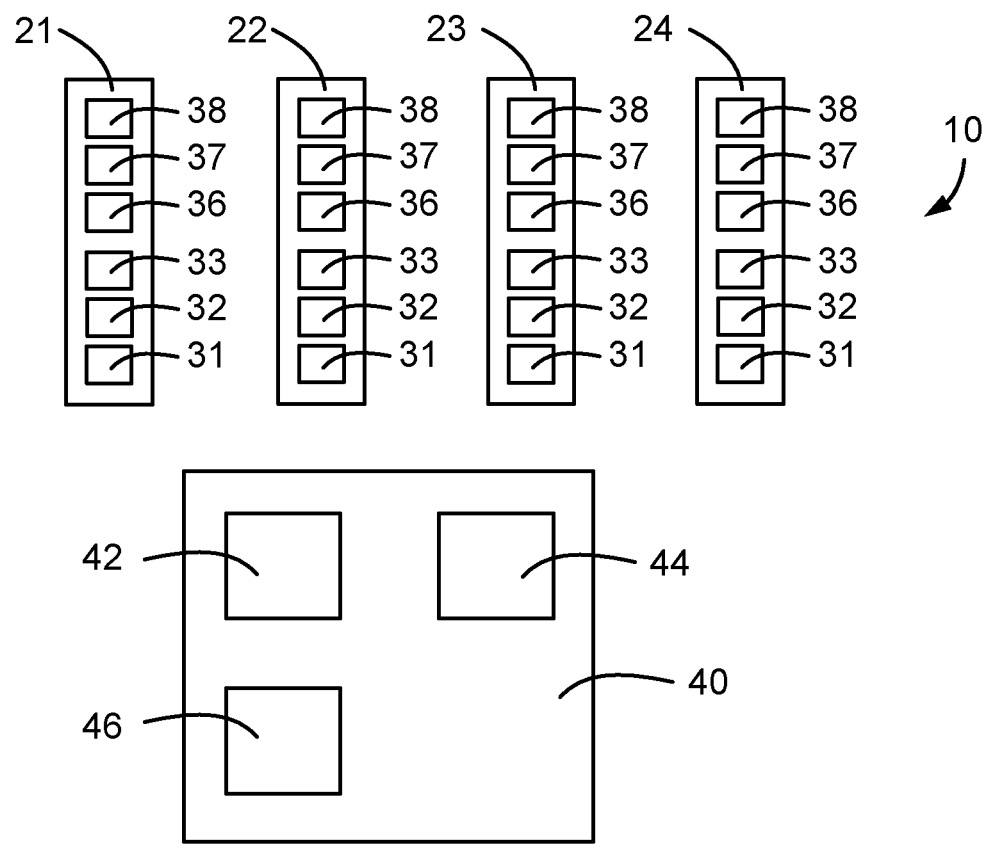
FIG. 1 diagrammatically shows a motion tracking system in accordance with an embodiment.

FIG. 1 diagrammatically shows a motion tracking system 10 in accordance with an embodiment. The motion tracking system 10 includes a plurality of sensors 21-24 and a computing apparatus 40.

The sensors 21-24 are MARG sensors that include a gyroscope 31, an accelerometer 32, and a magnetometer 33; in some other non-illustrated embodiments, the sensors do not include a magnetometer 33. The sensors 21-24 also include at least one processor 36 and at least one memory 37 for running a sensor fusion algorithm. In some embodiments such as the one of FIG. 1, the sensors 21-24 further include a first communications module 38 for transmitting and receiving data that enables the sensors 21-24 to transmit (through a wired or wireless communications technology and protocol known by a skilled person, for instance but without limitation, Bluetooth communications, cellular network communications such as GSM, UMTS or LTE, wireless LAN communications, etc.) measurements of each of the sensing devices 31-33 and/or measurements as provided by the sensor fusion algorithm to the computing apparatus 40. The same first communications modules 38 enable the sensors 21-24 to receive data from the computing apparatus 40. In less preferred embodiments, the sensors 21-24 are not provided with the first communications module 38; in these embodiments, data can be extracted from the sensors 21-24 and/or provided to the sensors 21-24 by means of a computer readable storage medium.

The computing apparatus 40 includes at least one processor 42 and at least one memory 44. Preferably, the computing apparatus 40 further includes a second communications module 46 for transmitting and receiving data. When the computing apparatus 40 is not provided with the second communications module 46, data can be extracted therefrom and/or introduced therein by means of a computer readable storage medium.

Figure 2A:
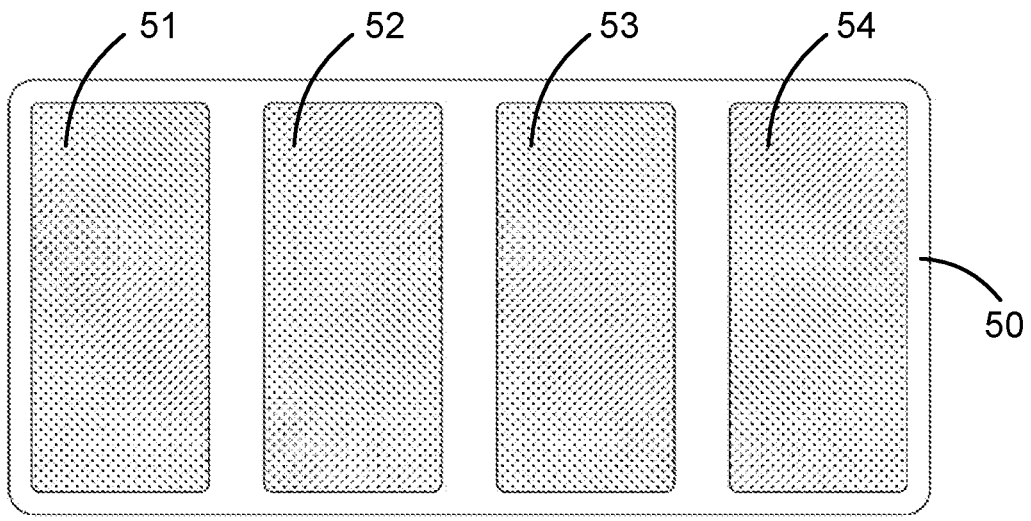
FIGS. 2A-2B show a holding device of a motion tracking system in accordance with an embodiment.
Figure 2B:
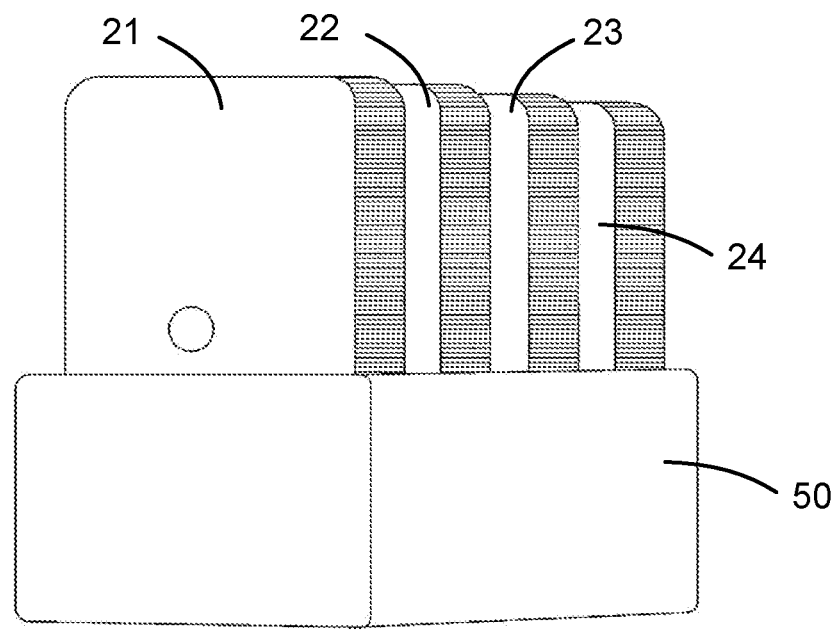

FIGS. 2A-2B show a holding device 50 of a motion tracking system in accordance with an embodiment.

The holding device 50 (also referred to as first device within the context of the present disclosure), which may be part of a motion tracking system such as the motion tracking system 10 of FIG. 1, comprises a plurality of cavities 51-54 adapted to receive the sensors 21-24 as illustrated in FIG. 3B.

In this example, the cavities 51-54 are dimensioned such that the sensors 21-24 may be introduced with a particular orientation thereof. The sensors 21-24 may fit tightly or with some play. The holding device 50 may be used for one or more of the following purposes: for storing the sensors 21-24 while the same are not in use, for determining whether the sensors 21-24 require to be calibrated, and/or even for calibrating the sensors 21-24 in a simple and effective manner, in which case the holding device 50 is rotated for calibrating the sensors 21-24 while they are introduced therein (depending on the type of rotation necessary for calibrating the sensors, it may be necessary to cover the sensors 21-24 with the hand during the calibration procedure so that they do not fall off from the holding device 50).

In some other examples, the holding device 50 comprises a single cavity or more than one cavity in which two or more sensors may be introduced side-by-side such that the two or more sensors have fixed relative orientations (so that each sensor does not change its orientation with respect to the other sensors). To this end, the cavity or cavities may include one or more spacing elements that provide a gap between each pair of sensors.

While the sensors 21-24 are introduced in the holding device 50 they are aligned and, thus, they may provide the first orientations to the computing apparatus as described with reference to the methods 100, 101 of FIGS. 3 and 4.

Figure 3:
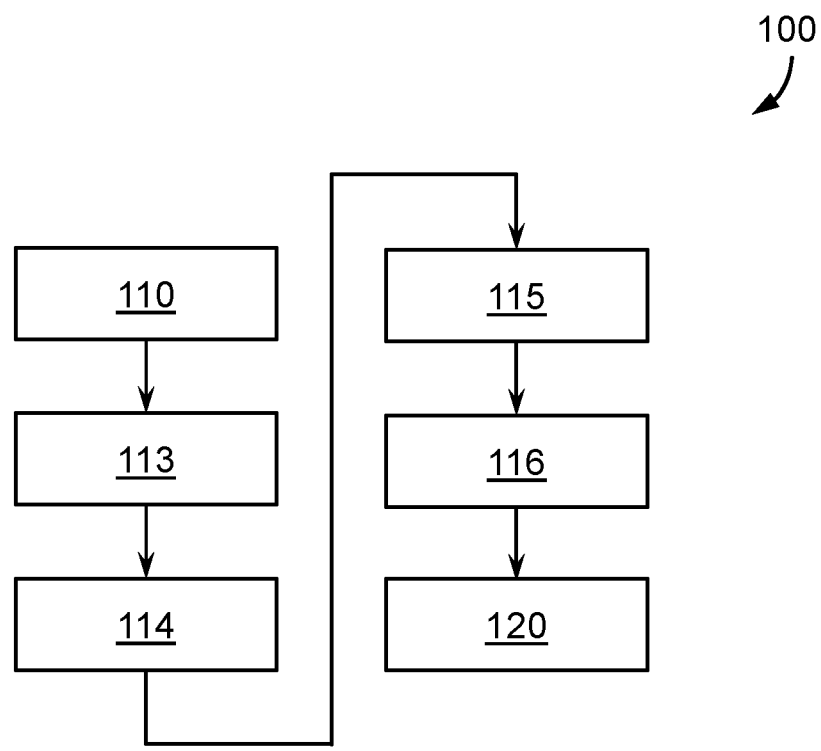
FIGS. 3-4 diagrammatically show methods in accordance with embodiments.

FIG. 3 diagrammatically shows a method 100 for adjusting operation of a motion tracking system, such as the motion tracking system 10 of FIG. 1.

The method 100 comprises a step of aligning 110 a plurality of sensors (e.g. the sensors 21-24 of the motion tracking system 10). The sensors may be aligned in a number of ways as will be apparent from the present disclosure to the person skilled in the art. The sensors shall be arranged in accordance with a known set of orientations of the sensors (for example a predetermined set of orientations), thereby making possible to determine the deviations between the actual heading of the sensors and the heading measured by the same; accordingly, the sensors need not to be facing the same direction even though this is preferable for simplicity and ease of use reasons.

The method 100 further comprises a step of providing 113, each sensor of the motion tracking system, a first orientation when the sensors are aligned in accordance with step 110. The first orientations, which comprise first headings of the sensors, are provided to a computing apparatus (e.g. the computing apparatus 40 of the motion tracking system 10).

The method 100 further comprises a step of placing 114 the sensors of the motion tracking system on a person so that motion thereof may be tracked.

The method 100 further comprises a step of providing 115, each sensor of the motion tracking system, a second orientation when the sensors are placed on the person. The second orientations, which comprise second headings of the sensors, are provided to the computing apparatus.

Preferably, the time elapsed between the step of providing 113 the first orientations and the step of providing 115 the second orientations is as short as possible, preferably less than 5 minutes, and more preferably less than 3 minutes and/or 1 minute, therefore preferably the sensors are placed 114 on the body in this time interval. By reducing the time it takes to carry out this process, the lower the error that affects the measurements of the sensors.

The method 100 further comprises a step of digitally determining 116, the computing apparatus of the motion tracking system, whether the sensors are placed on the person according to a predetermined sensor arrangement. In order to carry out such determination, the computing apparatus processes both the first and second headings of each sensor such that it computes the difference between the measured headings and the headings that are expected when the sensors are correctly placed on the person, in accordance with the predetermined sensor arrangement. In this regard, the first headings are indicative of the differences in heading of each sensor with respect to the other sensors, whereas the second headings are used for determining differences between the headings of each pair of sensors and the expected heading differences.

The method 100 further comprises a step of adjusting 120, the computing apparatus of the motion tracking system, the operation of the motion tracking system based on the determination made in step 116.

Figure 4:
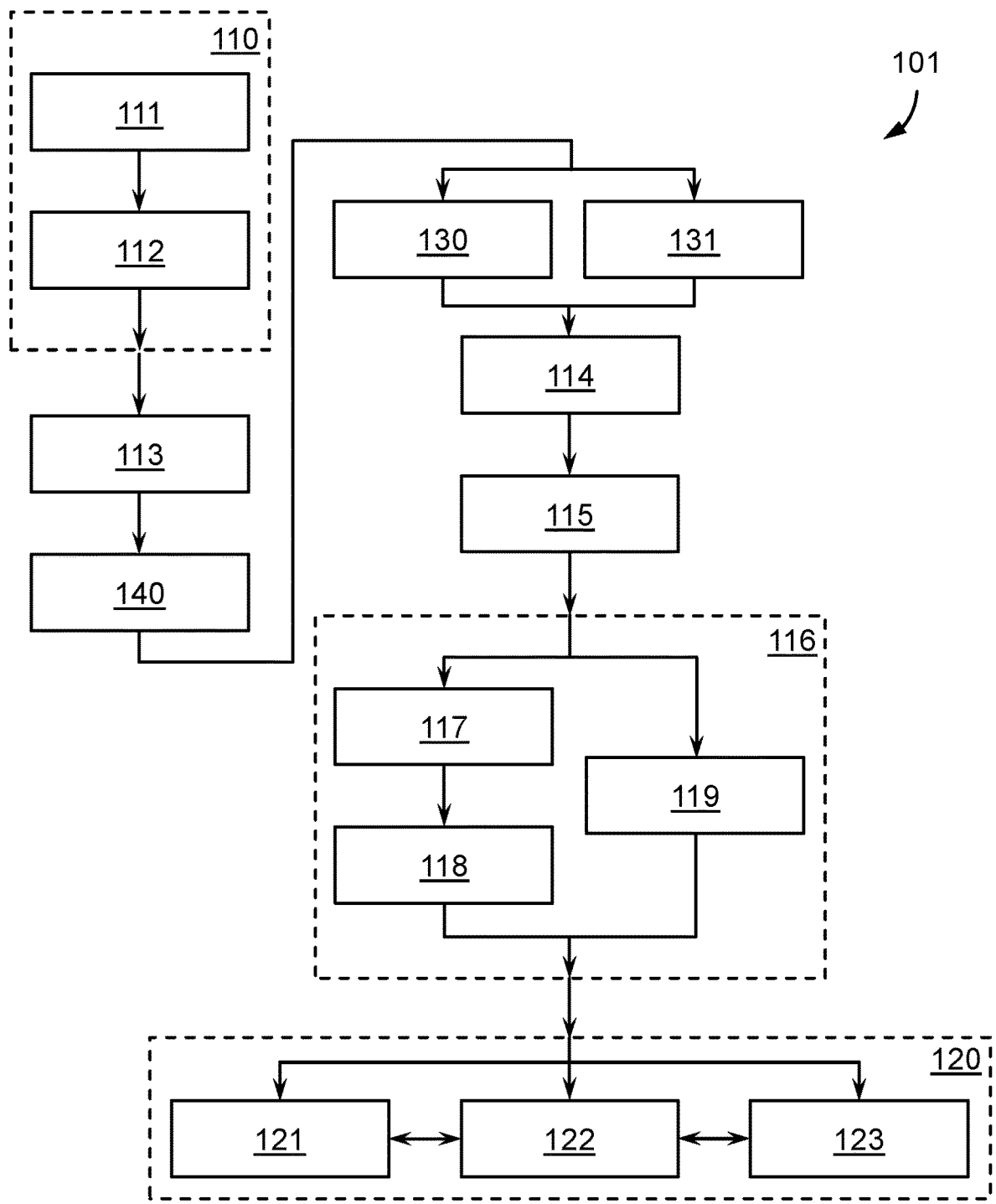

FIG. 4 diagrammatically shows a method 101 for adjusting operation of a motion tracking system, such as the motion tracking system 10 of FIG. 1.

The method 101 comprises the step of aligning 110 the plurality of sensors by means of: a step of providing 111 a first device (e.g. the holding device 50 of FIGS. 2A-2B) with at least one cavity adapted for introduction of one or more sensors (e.g. the sensors 21-24 of the motion tracking system 10); and a step of introducing 112 each sensor of the motion tracking system into the first device. When the sensors are in the first device, they have fixed relative orientations with respect to the other sensors owing to the at least one cavity. Since the fixed relative orientations are known, the sensors are aligned.

The method 101 further comprises the step of providing 113, each sensor of the motion tracking system, the first orientation when the sensors are aligned. In this case, the first orientations are provided while the sensors are introduced in the first device since that is when they are aligned.

The method 101 further comprises a step of digitally computing 140, the computing apparatus of the motion tracking system, a heading difference between each pair of first headings of the first orientations. To this end, the computing apparatus retrieves, for instance, an angle or a vector per pair of first headings, said angle or vector being indicative of the difference between the corresponding first headings. As the first orientations are provided while the sensors are aligned, these heading differences are indicative of the relative differences between the measurements of the sensors.

The computing apparatus digitally processes the computed heading differences of the first headings in order to determine if one or more sensors of the motion tracking system are aligned such that they have a 180° heading rotation with respect to the corresponding other sensor of the motion tracking system. The computing apparatus of the motion tracking system then carries out both the steps of digitally determining 116 whether the sensors of the motion tracking system are placed on the person according to the predetermined sensor arrangement and adjusting 120 the operation of the motion tracking system if each computed heading difference of the first headings fulfills the following: a modulus of the heading difference is less than or equal to a predetermined validation threshold; or a modulus of 180° minus the heading difference is less than or equal to the predetermined validation threshold.

In some embodiments, if at least one computed heading difference does not fulfill any one of said two criteria, the computing apparatus adjusts the operation of the motion tracking system such that it provides at least one user perceptible signal indicative of the computing apparatus having determined that at least one computed heading difference does not fulfill any one of the above criteria.

The method 101 further comprises a step of not processing 130 measurements of magnetometers in a sensor fusion algorithm of each sensor of the motion tracking system, or a step of reducing 131 a weight of the measurements of the magnetometers in the sensor fusion algorithm of each sensor of the motion tracking system. In particular, the computing apparatus commands the sensors to either not process 130 the measurements or reduce 131 the weight thereof in the sensor fusion algorithm so that the orientations provided when the sensors are on the person are not affected (or are less affected) by erroneous measurements of magnetometers; the computing apparatus commands the sensors to operate in this way while they are still aligned, for instance while being on a surface or introduced in the first device, thereby making the drift of the gyroscope the only or the main source of error in the orientations provided afterwards, which is mostly negligible thanks to the reduced drift error.

In some cases, the computing apparatus commands the sensors to function in that way even before the first orientations are provided 113, so that the same are not affected (or are less affected) by erroneous measurements of magnetometers.

The method 100 further comprises the step of placing 114 the sensors of the motion tracking system on a person.

The method 100 further comprises the step of providing 115 the second orientations when the sensors are placed on the person. As aforementioned, the computing apparatus may command the sensors to provide the second orientations after commanding them not to process 130 the measurements of the magnetometers or reduce 131 the weight thereof in the sensor fusion algorithm. In this way, the second orientations are provided without being influenced (or less influenced) by the measurements of the magnetometers.

The method 100 further comprises the step of digitally determining 116 whether the sensors are placed on the person according to the predetermined sensor arrangement.

The digital determination 116 is carried out by means of a first step whereby the computing apparatus of the motion tracking system digitally computes 117 a first transformation for each sensor of the motion tracking system that aligns the first heading thereof with a first predetermined heading, and a second step whereby the computing apparatus digitally processes 118 a third heading of each sensor of the motion tracking system in order to compute heading differences from all pairs of the third headings and determine whether the sensors are placed on the person according to the predetermined sensor arrangement, each third heading being the second heading of the corresponding sensor with the corresponding first transformation applied thereto.

Alternatively, the digital determination 116 is carried out by means of a step whereby the computing apparatus of the motion tracking system digitally processes 119 the second heading of each sensor of the motion tracking system in order to compute heading differences from all pairs of second headings and determine whether the sensors are placed on the person according to the predetermined sensor arrangement, the first heading of each sensor being processed such that it adjusts the corresponding heading differences computed or heading differences according to the predetermined sensor arrangement.

The method 100 further comprises the step of adjusting 120 the operation of the motion tracking system based on the determination made in step 116.

The adjustment 120 may be carried out by means of a step of digitally computing 121, the computing apparatus of the motion tracking system, a second transformation for each sensor of the motion tracking system that aligns the third heading thereof with a second predetermined heading for the corresponding sensor according to the predetermined sensor arrangement, and digitally applying, the computing apparatus, the second transformations or both the first and second transformations computed to each orientation provided by each sensor to the computing apparatus while motion of the person is tracked with the motion tracking system, or to an algorithm of the computing apparatus for processing the motion of the person tracked with the motion tracking system. These second transformations are computed and applied if steps 117 and 118 are carried out.

Additionally or alternatively, the adjustment 120 may be carried out by means of a step of providing 122 at least one user perceptible signal indicative of the computing apparatus having determined that at least one sensor of the motion tracking system is not placed on the person according to the predetermined sensor arrangement.

Additionally or alternatively, the adjustment 120 may be carried out by means of a step of digitally computing 123 a first transformation for each sensor that aligns the second heading thereof with a first predetermined heading for the corresponding sensor according to both the predetermined sensor arrangement and the first heading, and digitally applying the first transformations computed to each orientation provided by each sensor to the computing apparatus while motion of the person is tracked with the motion tracking system, or to an algorithm of the computing apparatus for processing the motion of the person tracked with the motion tracking system. These first transformations are computed and applied if step 119 is carried out.

Figure 5A:
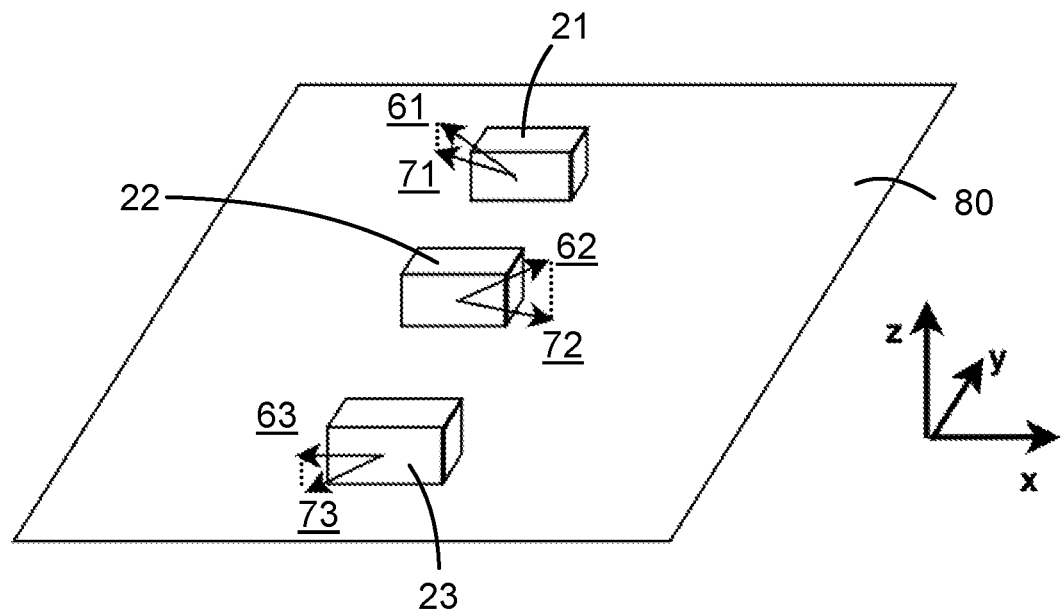
FIGS. 5A-5C diagrammatically show headings of sensors in accordance with orientations provided by the sensors.
Figure 5B:
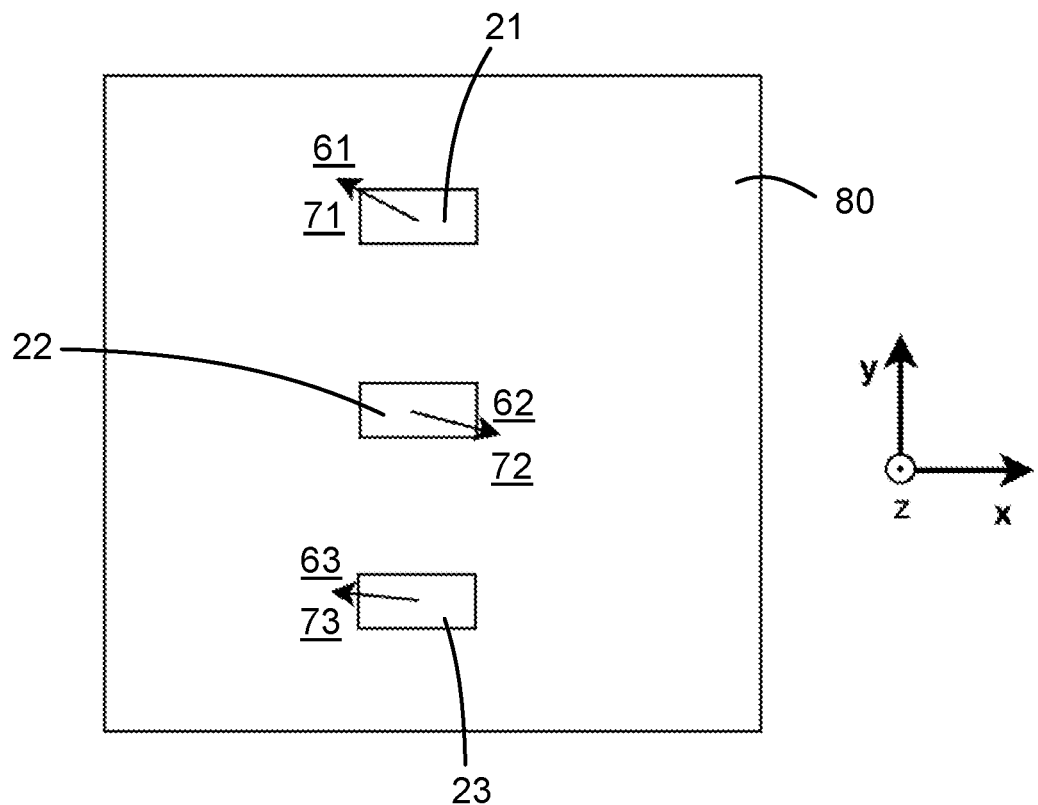
Figure 5C:
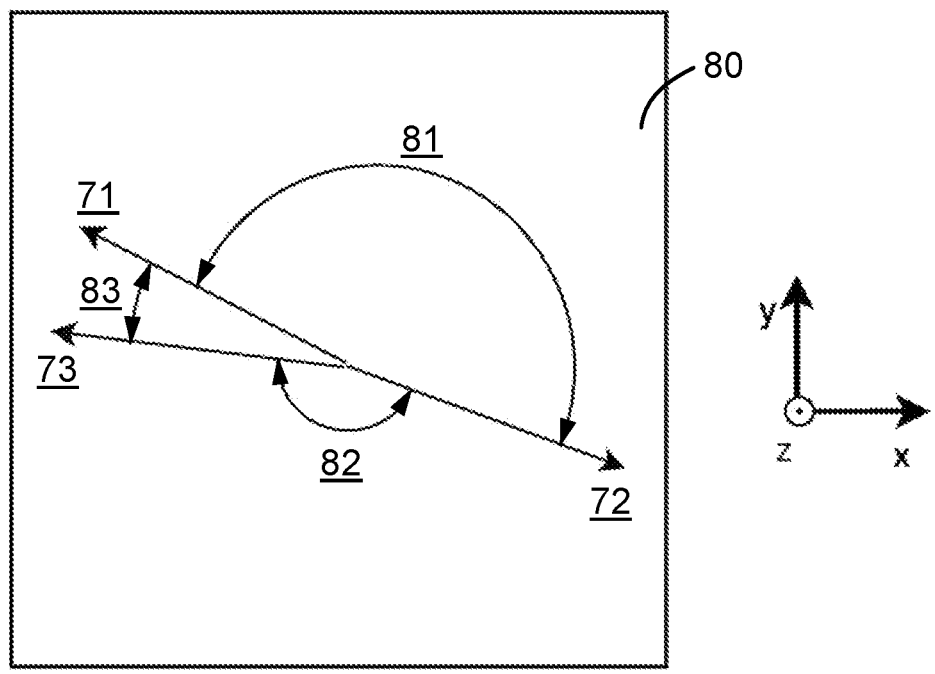

FIGS. 5A-5C diagrammatically show headings 71-73 of sensors 21-23 in accordance with orientations 61-63 provided by the sensors.

FIG. 5A shows, in a 3D view, the orientations and the headings, whereas FIG. 5B shows the same from a top view. FIG. 5C shows the heading differences between the headings 71-73 of the sensors 21-23. In all these figures, the orientations and headings are shown with vectors for the sake of clarity.

Each sensor 21-23 provides by means of the sensor fusion algorithms thereof an orientation 61-63, respectively, in an Earth's reference frame. The sensors 21-23 are aligned and are shown on top of a planar horizontal surface 80. Whereas the orientations 61-63 have components in all three axes (x, y, z) represented, the headings 71-73 (which are the projections of the orientations 61-63 on a horizontal plane corresponding, precisely, to the planar surface 80) have components in two axes (x, y). Accordingly, in the top view of FIG. 5B, each orientation 61-63 appears to overlap the corresponding heading 71-73.

With reference to FIG. 5C, the headings 71-73 are represented on the plane of the surface 80. In this example, three distinct heading differences may be computed: a first heading difference 81 between the heading 71 of a first sensor 21 and the heading 72 of a second sensor 22, a second heading difference 82 between the heading 72 of the second sensor 22 and a heading 73 of a third sensor 23, and a third heading difference 83 between the heading 71 of the first sensor 21 and the heading 73 of the third sensor 23. These heading differences 81-83 are represented as angular differences and reveal the differences in headings between the measurements of all the sensors 21-23 despite the same are aligned. In the context of the present disclosure, the headings 71-73 are also referred to as first headings.

In this case however, in addition to the errors in the measurements of the sensors 21-23, according to the headings 71-73, and in particular to the measured heading differences 81-83, it appears that the second sensor 22 (in the middle) is flipped 180° with respect to the other two sensors 21, 23. The first and second heading differences 81, 82 are greater than 150° and smaller than 210°, values which result from the range 180°±30°, where 30° is an exemplary predetermined validation threshold. Thus, in this example, the computing apparatus would determine that the deviations 81-83 between the headings 71-73 are acceptable and, thus, the sensors 21-23 may be placed on the body of a person for motion tracking thereof, and adjust the operation of the corresponding motion tracking system afterwards. The computing apparatus registers the headings 71-73 (i.e. first headings) so that it may compensate for the heading differences 81-83 between the sensors 21-23.

Figure 6A:
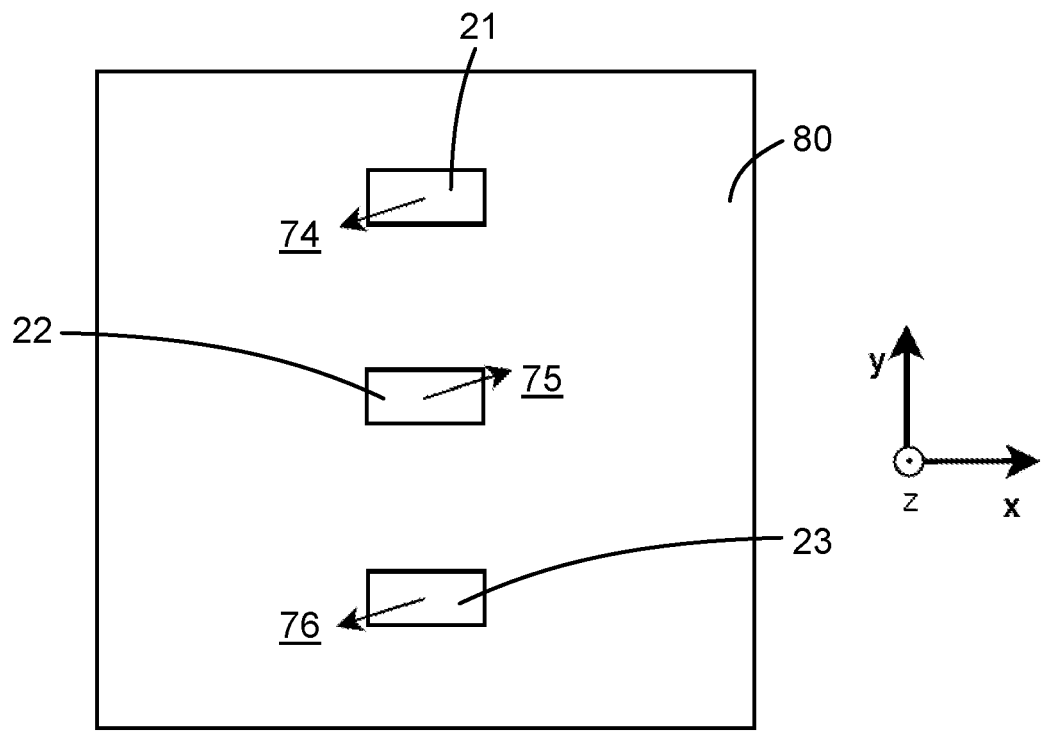
FIGS. 6A-6B diagrammatically show the headings of FIGS. 5A-5C after applying transformations that align them.
Figure 6B:
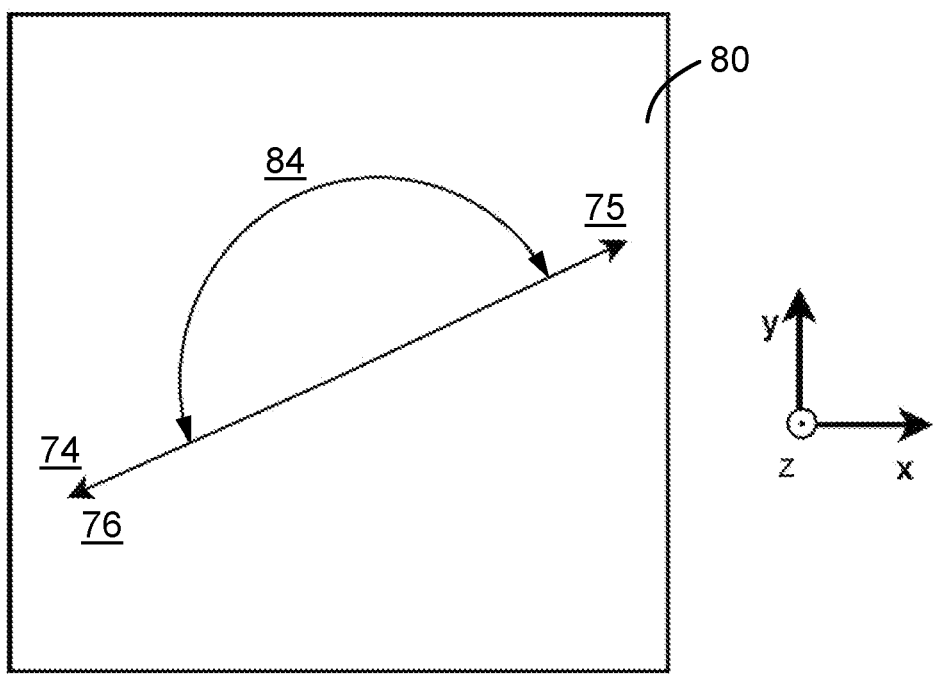

FIGS. 6A-6B diagrammatically show the headings 71-73 of FIGS. 5A-5C after applying transformations that aligns them.

The computing apparatus digitally computes transformations that align each of the registered headings 71-73 with a first predetermined heading. Accordingly, upon applying the transformations, adjusted headings 74-76 are provided. In this particular example, the heading 75 of the second sensor 22 is aligned such that it forms a 180° heading difference 84 with respect to the adjusted headings 74, 76 of the first and third sensors 21, 23, even though in other examples all the headings 74-76 may be adjusted such that no heading difference exists between any pair of the headings 74-76, such as between the headings 74 and 76 of this example.

With the applied transformations the headings are virtually aligned, thus upon placing the sensors on the body, such as described with reference to FIGS. 7A-7C and 8A-8B, the computing apparatus may determine whether the sensors are placed according to a predetermined sensor arrangement.

Figure 7A:
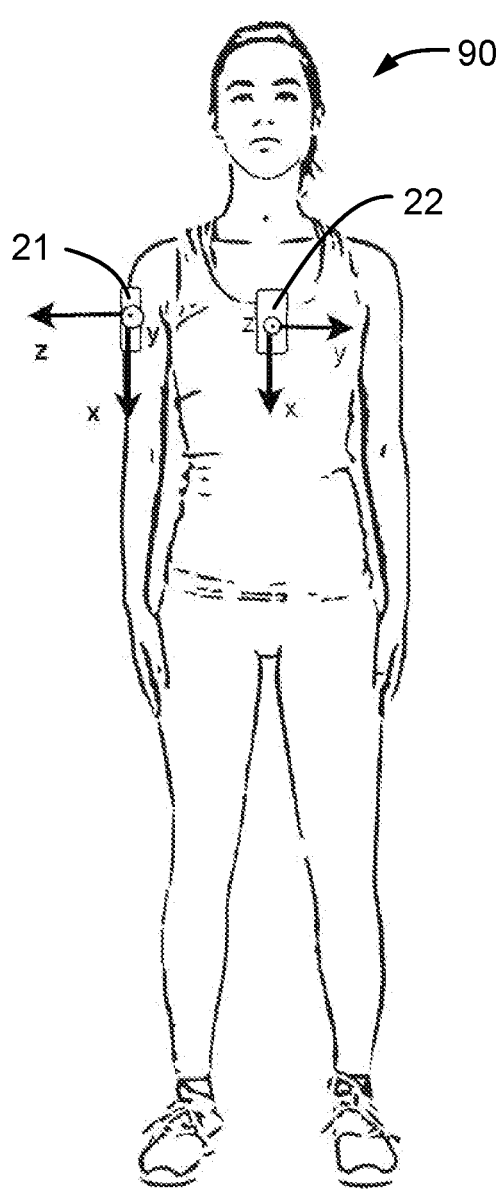
FIGS. 7A-7C and 8A-8B diagrammatically show a person having sensors placed thereon and the heading differences resulting therefrom.
Figure 7B:
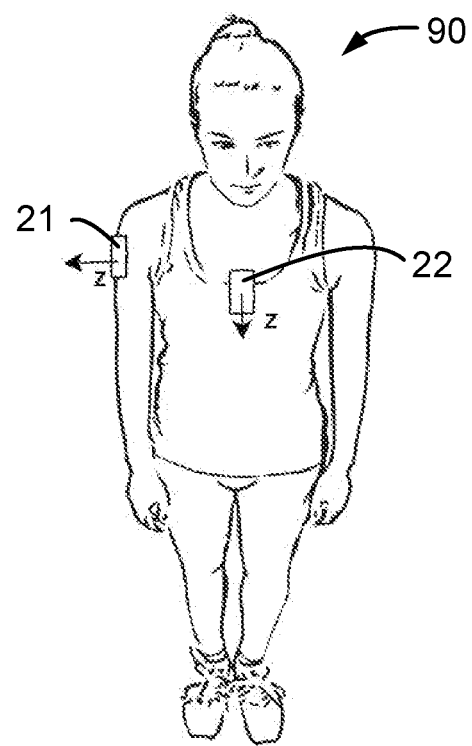
Figure 7C:
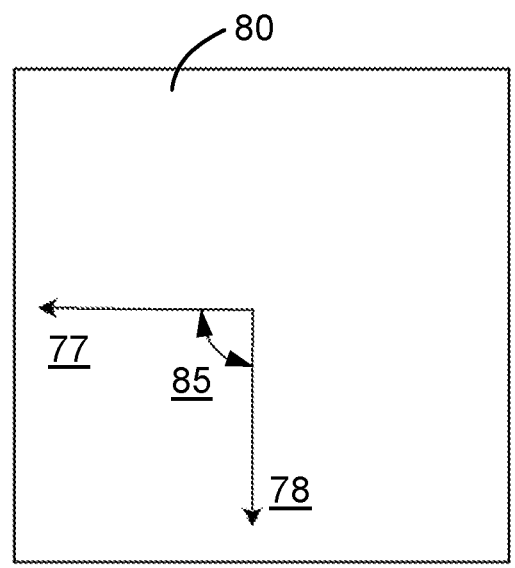

FIGS. 7A-7C diagrammatically show a person 90 having sensors 21, 22 placed thereon and the heading difference 85 resulting therefrom. Illustrated in FIGS. 7A and 7B are the reference axes of the sensors 21, 22 for the sake of clarity. FIG. 7A shows the person 90 from a front-facing view, whereas FIG. 7B shows the person 90 from an elevated view.

The person 90 is standing still, for instance according to a predetermined posture. A first sensor 21 is placed on the upper arm, particularly on a side thereof, whereas a second sensor 22 is placed on the chest of the person 90. This placement of sensors 21, 22 corresponds to a particular predetermined sensor arrangement in which it is defined that the heading difference between the first and second sensors is 90°. As seen in FIG. 7C, the heading 77 of the first sensor 21 and the heading 78 of the second sensor 22, which are represented on a plane 80 corresponding to a horizontal, are such that the heading difference 85 thereof is of 90°. Therefore, a computing apparatus determines that the first and second sensors 21, 22 are placed on the person 90 according to the predetermined sensor arrangement.

Figure 8A:
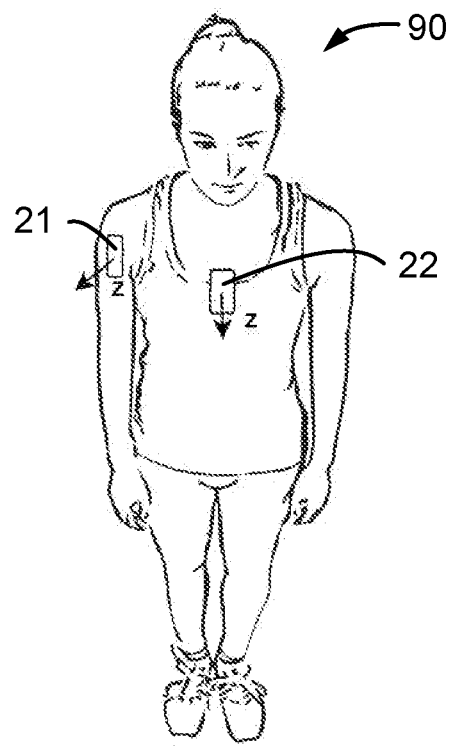
Figure 8B:
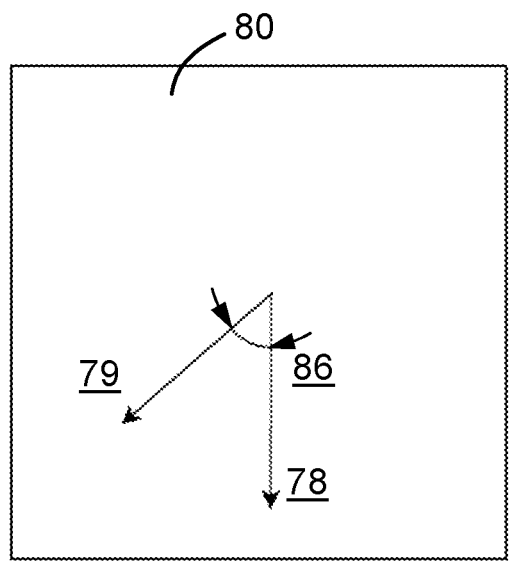

FIGS. 8A-8B diagrammatically show the person 90 having sensors 21, 22 placed thereon and the heading difference 86 resulting therefrom.

In this case, the predetermined sensor arrangement is the same of FIGS. 7A-7C, that is, the predetermined sensor arrangement defines or makes derivable that the heading difference between headings 79, 78 of the first and second sensors 21, 22 shall be of 90°. However, in this example the person has placed the sensors incorrectly. In particular, the first sensor 21 has been placed inwards and not completely perpendicular to the second sensor 22, which is on the chest of the person 90. The heading 79 of the first sensor 21 thus is different from the heading 77 as processed in the example of FIGS. 7A-7C. This, in turn, results in the heading difference 86 that is less than 90°. Depending upon the predetermined difference threshold or the pair of predetermined difference thresholds, this deviation from the expected heading difference (i.e. 90°) may result in the determination that the sensors are not correctly placed on the person 90. By way of example, if the predetermined difference threshold is 5°, as the heading difference 86 is not within the range 90° 5°, it is determined that the sensors are not placed according to the predetermined sensor arrangement. As another example, if there is a pair of predetermined difference thresholds that is −10° and 5°, as the heading difference 86 is not within the range [90° minus 10°, 90° plus 5°], it is determined that the sensors are not placed according to the predetermined sensor arrangement.

In this text, the term "comprises" and its derivations (such as "comprising", etc.) should not be understood in an excluding sense, that is, these terms should not be interpreted as excluding the possibility that what is described and defined may include further elements, steps, etc.

Even though the terms first, second, third, etc. have been used herein to describe several devices, parameters or variables, it will be understood that the devices, parameters or variables should not be limited by these terms since the terms are only used to distinguish one device, parameter or variable from another. For example, the first heading could as well be named second heading, and the second heading could be named first heading without departing from the scope of this disclosure.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A method for adjusting a motion tracking system comprising:
   determining, by a computing apparatus, a first orientation for each sensor of a plurality of sensors that are aligned on a planar surface prior to being placed on a person, wherein each of the plurality of sensors comprises a gyroscope and an accelerometer;
   computing, by the computing apparatus, one or more deviations in measurements of the plurality of sensors based on the first orientation determined for each of the plurality of sensors when the plurality of sensors are aligned on the planar surface prior to being placed on the person;

determining, by the computing apparatus and based on the one or more deviations in measurements computed when the plurality of sensors are aligned on the planar surface prior to being placed on the person, transformations that compensate for the one or more deviations;

outputting, by the computing apparatus, instructions to the person to place the plurality of sensors on different body parts of the person;

after the plurality of sensors are placed on the person, determining, by the computing apparatus, corresponding second orientations for the plurality of sensors;

applying, by the computing apparatus, the transformations that compensate for the one or more deviations to the corresponding second orientations to obtain transformed second orientations;

determining, by the computing apparatus and based at least partially on the transformed second orientations, that one or more of the plurality of sensors is incorrectly placed on the person according to a predetermined sensor arrangement that defines how the plurality of sensors are to be placed relative to each other on the different body parts of the person, wherein a first sensor of the plurality of sensors is determined to be incorrectly placed on the person according to the predetermined sensor arrangement based on a heading difference between the first sensor and at least one other sensor of the plurality of sensors; and adjusting, by the computing apparatus, operation of the motion tracking system using at least the transformations that are based on the one or more deviations in measurements to compensate for the one or more deviations in measurements while the motion tracking system tracks a motion of the person.

2. The method of claim 1, wherein, for each sensor of the plurality of sensors, the first orientation comprises a first beading, and respective ones of the transformations adjust respective second headings of the corresponding second orientations in accordance with the one or more deviations.

3. The method of claim 1, further comprising providing a signal indicative of the computing apparatus having determined that the one or more of the plurality of sensors is incorrectly placed on the person according to the predetermined sensor arrangement.

4. The method of claim 1, wherein the motion tracking system is calibrated without using magnetometer measurements.

5. The method of claim 1, wherein each sensor of the plurality of sensors further comprises a magnetometer; and
the method further includes, prior to the plurality of sensors being placed on the person:
adjusting at least one sensor fusion algorithm to exclude processing of measurements of the magnetometers of the plurality of sensors.

6. The method of claim 1, wherein the plurality of sensors are aligned on the planar surface by operations comprising:
providing a device adapted for introduction of one or more sensors of the plurality of sensors; and
introducing each sensor of the plurality of sensors into the device.

7. A motion tracking system comprising:
(a) a computing apparatus comprising at least one processor and at least one memory; and
(b) a plurality of sensors configured to provide, to the computing apparatus, orientation data, each sensor comprising a gyroscope and an accelerometer; and
the computing apparatus is programmed to:

determine a first orientation for each sensor of the plurality of sensors that are aligned on a planar surface prior to being placed on a person;

compute one or more deviations in measurements of the plurality of sensors based on the first orientation determined for each of the plurality of sensors when the plurality of sensors are aligned on the planar surface prior to being placed on the person;

determine, based on the one or more deviations in measurements computed when the plurality of sensors are aligned on the planar surface prior to being placed on the person, transformations that compensate for the one or more deviations;

output instructions to the person to place the plurality of sensors on different body parts of the person;

after the plurality of sensors are placed on the person, determine corresponding second orientations for the plurality of sensors;

apply the transformations that compensate for the one or more deviations to the corresponding second orientations to obtain transformed second orientations;

determine, based at least partially on the transformed second orientations, that one or more of the plurality of sensors is incorrectly placed on the person according to a predetermined sensor arrangement that defines how the plurality of sensors are to be placed relative to each other on the different body parts of the person, wherein a first sensor of the plurality of sensors is determined to be incorrectly placed on the person according to the predetermined sensor arrangement based on a heading difference between the first sensor and at least one other sensor of the plurality of sensors; and adjust operation of the motion tracking system using at least the transformations that are based on the one or more deviations in measurements to compensate for the one or more deviations in measurements while the motion tracking system tracks a motion of the person.

8. A method for adjusting operation of a motion tracking system comprising a computing apparatus and a plurality of sensors, each sensor comprising a gyroscope and an accelerometer, the method comprising:

determining, by the computing apparatus, a first orientation of each of the plurality of sensors that are aligned on a planar surface prior to being placed on a person;

outputting, by the computing apparatus, instructions to the person to place the plurality of sensors on different body parts of the person;

after the plurality of sensors are placed on the person, determining, by the computing apparatus, a second orientation of each of the plurality of sensors;

applying, by the computing apparatus, transformations to the second orientations of the plurality of sensors to obtain transformed second orientations, wherein the transformations compensate for one or more deviations in measurements computed using the first orientation of each of the plurality of sensors when the plurality of sensors are aligned on the planar surface prior to being placed on the person;

determining, by the computing apparatus, that one or more of the plurality of sensors is incorrectly placed on the person according to a predetermined sensor arrangement by using at least the transformed second orientations of the plurality of sensors, wherein the predetermined sensor arrangement defines how the plurality of sensors are to be placed relative to each other on the different body parts of the person, wherein a first sensor of the plurality of sensors is determined to be incorrectly placed on the person according to the predetermined sensor arrangement based on a heading difference between the first sensor and at least one other sensor of the plurality of sensors; and adjusting, by the computing apparatus, operation of the motion tracking system based on the determination that the one or more of the plurality of sensors is incorrectly placed on the different body parts of the person according to the predetermined sensor arrangement to compensate for the one or more deviations in measurements while the motion tracking system tracks a motion of the person.

9. The method of claim 8, wherein the plurality of sensors are aligned according to a predetermined alignment on the planar surface prior to being placed on the person.

10. The method of claim 8, wherein the operation of the motion tracking system is adjusted by applying respective ones of the transformations to corresponding second orientations of the plurality of sensors while the motion tracking system tracks the motion of the person.

11. The method of claim 10, wherein, for each sensor of the plurality of sensors, the first orientation comprises a first heading, and the respective ones of the transformations adjust respective second headings of the corresponding second orientations in accordance with the one or more deviations.

12. The method of claim 8, wherein each sensor of the plurality of sensors further comprises a magnetometer; and
the method further includes, prior to the plurality of sensors being placed on the person:
adjusting at least one sensor fusion algorithm to exclude processing of measurements of the magnetometers of the plurality of sensors.

13. The method of claim 8, wherein the plurality of sensors are aligned on the planar surface by operations comprising:
providing a device adapted for introduction of one or more sensors of the plurality of sensors; and
introducing each sensor of the plurality of sensors into the device.

14. The motion tracking system of claim 7, wherein, for each sensor of the plurality of sensors, the first orientation comprises a first heading, and respective ones of the transformations adjust respective second headings of the corresponding second orientations in accordance with the one or more deviations.

15. The motion tracking system of claim 7, wherein the computing apparatus is further programmed to provide a signal indicative of the computing apparatus having determined that the one or more of the plurality of sensors is incorrectly placed on the person according to the predetermined sensor arrangement.

16. The method of claim 1, wherein each sensor of the plurality of sensors further comprises a magnetometer, and the method further includes, prior to the plurality of sensors being placed on the person:
adjusting at least one sensor fusion algorithm to reduce a weight of measurements of the magnetometers in the at least one sensor fusion algorithm.

17. The method of claim 8, wherein each sensor of the plurality of sensors further comprises a magnetometer; and
the method further includes, prior to the plurality of sensors being placed on the person:
adjusting at least one sensor fusion algorithm to reduce a weight of measurements of the magnetometers in the at least one sensor fusion algorithm.

18. The motion tracking system of claim 7, wherein each sensor of the plurality of sensors further comprises a magnetometer; and
the motion tracking system is configured to, prior to the plurality of sensors being placed on the person:
adjust at least one sensor fusion algorithm to exclude processing of measurements of the magnetometers of the plurality of sensors; or
adjust the at least one sensor fusion algorithm to reduce a weight of the measurements of the magnetometers in the at least one sensor fusion algorithm.

* * * * *

UNITED STATES PATENT AND TRADEMARK OFFICE
CERTIFICATE OF CORRECTION

PATENT NO. : 12,318,190 B2  
APPLICATION NO. : 17/824742  
DATED : June 3, 2025  
INVENTOR(S) : Ungaro Pinto Coelho et al.

Page 1 of 1

It is certified that error appears in the above-identified patent and that said Letters Patent is hereby corrected as shown below:

In the Claims

In Column 23, Line 37, in Claim 2, delete "beading," and insert --heading,-- therefor In Column 26, Line 14, in Claim 16, delete "magnetometer," and insert --magnetometer;-- therefor Signed and Sealed this  
Tenth Day of February, 2026

John A. Squires  
*Director of the United States Patent and Trademark Office*